(12) United States Patent
Takadama et al.

(10) Patent No.: US 10,617,345 B2
(45) Date of Patent: Apr. 14, 2020

(54) SLEEP STAGE ESTIMATING APPARATUS, BIOLOGICAL DATA ESTIMATING APPARATUS, SLEEP STAGE ESTIMATING METHOD, AND BIOLOGICAL DATA ESTIMATING METHOD

(71) Applicant: The University of Electro-Communications, Tokyo (JP)

(72) Inventors: Keiki Takadama, Tokyo (JP); Tomohiro Harada, Tokyo (JP)

(73) Assignee: The University of Electro-Communications, Tokyo (JP)

( * ) Notice: Subject to any disclaimer, the term of this patent is extended or adjusted under 35 U.S.C. 154(b) by 152 days.

(21) Appl. No.: 15/558,321

(22) PCT Filed: Mar. 14, 2016

(86) PCT No.: PCT/JP2016/058031
§ 371 (c)(1),
(2) Date: Sep. 14, 2017

(87) PCT Pub. No.: WO2016/148111
PCT Pub. Date: Sep. 22, 2016

(65) Prior Publication Data
US 2018/0064389 A1  Mar. 8, 2018

(30) Foreign Application Priority Data
Mar. 18, 2015 (JP) .................. 2015-055080

(51) Int. Cl.
*A61B 5/02* (2006.01)
*A61B 5/00* (2006.01)
(Continued)

(52) U.S. Cl.
CPC ............ *A61B 5/4812* (2013.01); *A61B 5/002* (2013.01); *A61B 5/02108* (2013.01);
(Continued)

(58) Field of Classification Search
CPC ... A61B 5/4812; A61B 5/4815; A61B 5/7278; A61B 5/02108; A61B 5/02
See application file for complete search history.

(56) References Cited

FOREIGN PATENT DOCUMENTS

| JP | 2003-079587 | 3/2003 |
|----|-------------|--------|
| JP | 2014-239789 | 12/2014 |

OTHER PUBLICATIONS

Matsushima et al., Sleep Stage Estimation by Evolutionary Computation Using Heartbeat Data and Body-Movement, Dec. 2012, International Journal of Advancements in Computing Technology (IJACT), vol. 4, No. 22, pp. 281-290 (Year: 2012).*
(Continued)

*Primary Examiner* — Toan M Le
(74) *Attorney, Agent, or Firm* — IPUSA, PLLC (57) ABSTRACT

The estimation of the sleep stage at a time point where data does not exist, is enabled. An acquiring unit configured to acquire biological data indicating a wave of a heartbeat; a parameter estimating unit configured to estimate a parameter by using the biological data, with respect to a mathematical expression defining a medium frequency component of the wave of the heartbeat by using the parameter; and a sleep stage estimating unit configured to estimate a sleep stage from a value of the medium frequency component at any time point, based on the mathematical expression to which the estimated parameter is applied, are included.

9 Claims, 10 Drawing Sheets

(51) Int. Cl.
*A61B 5/021* (2006.01)
*A61B 5/11* (2006.01)
*A61B 5/08* (2006.01)

(52) U.S. Cl.
CPC .......... *A61B 5/0816* (2013.01); *A61B 5/1116* (2013.01); *A61B 5/6891* (2013.01); *A61B 5/7278* (2013.01); *A61B 5/4815* (2013.01); *A61B 5/7246* (2013.01); *A61B 2505/07* (2013.01); *A61B 2505/09* (2013.01); *A61B 2562/0247* (2013.01); *A61B 2562/046* (2013.01)

(56) References Cited

OTHER PUBLICATIONS

Rechtschaffen, A. and Kales, A. (Eds.): A Manual of Standardized Terminology, Techniques and Scaring System for Sleep Stage of Human Subjects, Public Health Service U.S.Government Printing Office (1968).

T.Watanabe, and K.Watanabe: "Noncontact Method for Sleep Stage Estimation", IEEE Transaction on Biomedical Engineering, No. 10,vol. 51, pp. 1735-1748, 2004.

Matsushima, H., Hirose, K., Hattori, K., Sato, H., and Takadama, K.: "Sleep Stage Estimation by Evolutionary Computation Using Heartbeat Data and Body-Movement", Proceeding of the 15th Asia Pacific Symposium on Intelligent and Evolutionary Systems, pp. 103-110, 2011.

Tajima, Y., Nakata, M., and Takadama, K.: "Personalized real-time sleep stage remote monitoring system", The Eighth International Symposium on Medical Information and Communication Technology (ISMICT 2014), 2014.

R. M. Harper, V. L.Schechman and K. A. Kluge: "Machine classification of infant sleep state using cardiorespiratory measures", Electro encephalogr. Clini. Neurophysiol., No. 67, pp. 379-387, 1987.

K. Otsuka, Y. Ichimaru and T. Yanaga: "Studies of arrthythmias by 24-hour polygraphic records. II. relationship between heart rate and sleep stages", Fukuoka Acta. Med., vol. 72, No. 10, pp. 589-595, 1991.

International Search Report for PCT/JP2016/058031 dated Jun. 14, 2016.

* cited by examiner

DEFINITION EXPRESSION OF WAVE OF HEARTBEAT $$f(t) = c + \sum_{n=1}^{N}\left(a_n \cos\frac{2\pi t}{L/n} + b_n \sin\frac{2\pi t}{L/n}\right)$$

CALCULATION EXPRESSION OF PARAMETER $$\begin{pmatrix} c \\ a_1 \\ \vdots \\ a_N \\ b_1 \\ \vdots \\ b_N \end{pmatrix} = \begin{pmatrix} \sum_{t=1}^{T} 1 & \sum_{t=1}^{T}\cos m_1 t & \sum_{t=1}^{T}\cos m_2 t & \cdots & \sum_{t=1}^{T}\cos m_N t & \sum_{t=1}^{T}\sin m_1 t & \cdots & \sum_{t=1}^{T}\sin m_N t \\ \sum_{t=1}^{T}\cos m_1 t & \frac{\lambda T}{N} + \sum_{t=1}^{T}\cos m_1 t \cos m_1 t & \sum_{t=1}^{T}\cos m_1 t \cos m_2 t & \cdots & \sum_{t=1}^{T}\cos m_1 t \cos m_N t & \sum_{t=1}^{T}\cos m_1 t \sin m_1 t & \cdots & \sum_{t=1}^{T}\cos m_1 t \sin m_N t \\ \sum_{t=1}^{T}\cos m_2 t & \sum_{t=1}^{T}\cos m_2 t \cos m_1 t & \frac{\lambda T}{N} + \sum_{t=1}^{T}\cos m_2 t \cos m_2 t & & & & & \\ \vdots & & & \ddots & & & & \vdots \\ \sum_{t=1}^{T}\cos m_N t & & & & & & & \\ \sum_{t=1}^{T}\sin m_1 t & & & & & & & \\ \vdots & & & & & & \ddots & \\ \sum_{t=1}^{T}\sin m_N t & \sum_{t=1}^{T}\sin m_N t \cos m_1 t & & & & & & \frac{\lambda T}{N} + \sum_{t=1}^{T}\sin m_N t \sin m_N t \end{pmatrix}^{-1} \begin{pmatrix} \sum_{t=1}^{T} HR(t) \\ \sum_{t=1}^{T} HR(t)\cos m_1 t \\ \vdots \\ \sum_{t=1}^{T} HR(t)\cos m_N t \\ \sum_{t=1}^{T} HR(t)\sin m_1 t \\ \vdots \\ \sum_{t=1}^{T} HR(t)\sin m_N t \end{pmatrix}$$

$$m_i = \frac{2\pi}{L/i}$$

FIG.4

DEFINITION EXPRESSION OF WAVE OF HEARTBEAT $$f(t) = c + \sum_{n=1}^{N}\left(a_n \cos\frac{2\pi t}{L/n} + b_n \sin\frac{2\pi t}{L/n}\right)$$

LIKELIHOOD FUNCTION $$J = \frac{1}{T}\sum_{t=1}^{T}(HR(t) - f(t))^2 + \frac{\lambda}{N}\left(\sum_{n=1}^{N}(a_n^2 + b_n^2)\right)$$

PARTIAL DIFFERENTIATION OF
LIKELIHOOD FUNCTION BY PARAMETER $$\frac{\partial J}{\partial c} = \frac{2}{T}\sum_{t=1}^{T}(HR(t) - f(t)) = 0$$

$$\frac{\partial J}{\partial a_i} = \frac{2}{T}\sum_{t=1}^{T}\cos m_i\, t(HR(t) - f(t)) + \frac{2\lambda}{N}a_i = 0 \qquad m_i = \frac{2\pi}{L/i}$$

$$\frac{\partial J}{\partial b_i} = \frac{2}{T}\sum_{t=1}^{T}\sin m_i\, t(HR(t) - f(t)) + \frac{2\lambda}{N}b_i = 0$$

DETERMINANT OF SOLUTION OF PARAMETER

CALCULATION EXPRESSION
OF SLEEP STAGE $$average = \frac{1}{L}\sum_{t=1}^{L} f(t)$$

$$stdev = \sqrt{\frac{1}{L-1}\sum_{t=1}^{L}(average - f(t))^2}$$

$$sleep\ stage(t) = \begin{cases} 5 & f(t) > average + 2 \cdot stdev \\ 0 & f(t) < average - 2 \cdot stdev \\ \left\lfloor \frac{f(t) - average}{stdev} + 3 \right\rfloor & otherwise \end{cases}$$

SLEEP STAGE ESTIMATING APPARATUS, BIOLOGICAL DATA ESTIMATING APPARATUS, SLEEP STAGE ESTIMATING METHOD, AND BIOLOGICAL DATA ESTIMATING METHOD

TECHNICAL FIELD

The present invention relates to a technology of estimating a sleep stage.

BACKGROUND ART

Recently, the number of people suffering from sleep disorders including chronic insomnia has become significant, and traffic accidents caused by dozing are also frequent. Furthermore, although it is required to reduce the work load of nursing care for the elderly, with respect to the aging society which is rapidly advancing, it is not easy to reduce the work load due to resistance such as an elderly person wandering late at night that cannot be predicted, and erroneous timings of changing diapers of an elderly person and calling an elderly person to wake up. There is a possibility that these circumstances can be improved by properly determining the state of sleep and making actions appropriately.

As a method for estimating the sleep stage, a sleep polygraph test based on international standards for sleep stage classification by Rechtschaffen & Kales is known (Non Patent Literature 1). In this method, a special instrument is attached to a subject lying in a bed, data of EEG (electroencephalogram), EMG (electromyogram), and EOG (eye movement) are acquired, and the sleep stage is determined based on the expertise and the experience of the a doctor. However, to wear a special instrument is a heavy load on the subject, particularly, it is unrealistic for an elderly person to wear a special instrument all night.

Therefore, there has been proposed a method of measuring data of the body (heartbeat, respiration, and body movement) without directly attaching an instrument to the subject, and acquiring, from the measured data, data that can be approximated to the temporal transition data of sleep stages obtained by a sleep polygraph test. For example, Watanabe et al. have developed an unrestrained air mattress type sensor capable of measuring body data (heartbeat, respiration, and body movement), and have devised a method of determining the sleep stage from the obtained data (Patent Literature 1, Non Patent Literature 2).

Furthermore, Takadama et al. have devised a method of estimating the sleep stage by appropriately filtering data of the heartbeat obtained from an unrestrained type sensor (Non Patent Literature 3, Patent Literature 2, and Non Patent Literature 4).

Note that the principle of estimating the sleep stage from the data of the heartbeat is based on a number of findings indicating that there is a strong correlation between the medium frequency component of the heartbeat and the sleep stage (Non Patent Literature 5, Non Patent Literature 6).

CITATION LIST

Patent Literature

[PTL 1]
Japanese Unexamined Patent Application Publication No. 2003-079587

[PTL 2]
Japanese Unexamined Patent Application Publication No. 2014-239789

Non Patent Literature

[NPL 1]
Rechtschaffen, A. and Kales, A. (Eds.): A Manual of Standardized Terminology, Techniques and Scaring System for Sleep Stage of Human Subjects, Public Health Service U.S. Government Printing Office (1968)

[NPL 2]
T. Watanabe, and K. Watanabe: "Noncontact Method for Sleep Stage Estimation", IEEE TRANSACTION ON BIOMEDICAL ENGINEERING, No. 10, Vol. 51, pp. 1735-1748, 2004

[NPL 3]
Matsushima, H., Hirose, K., Hattori, K., Sato, H., and Takadama, K.: "Sleep Stage Estimation By Evolutionary Computation Using Heartbeat Data and Body-Movement", Proceeding of The 15th Asia Pacific Symposium on Intelligent and Evolutionary Systems, pp. 103-110, 2011

[NPL 4]
Tajima, Y., Nakata, M., and Takadama, K.: "Personalized real-time sleep stage remote monitoring system", The Eighth International Symposium on Medical Information and Communication Technology (ISMICT 2014), 2014

[NPL 5]
R. M. Harper, V. L. Schechman and K. A. Kluge: "Machine classification of infant sleep state using cardiorespiratory measures", Electro encephalogr. Clini. Neurophysiol., no. 67, pp. 379-387, 1987

[NPL 6]
K. Otsuka, Y. Ichimaru and T. Yanaga: "Studies of arrthythmias by 24-hour polygraphic records. II. relationship between heart rate and sleep stages", Fukuoka Acta. Med., vol. 72, no. 10, pp. 589-596, 1991

SUMMARY OF INVENTION

Technical Problem

The method of estimating the sleep stage from the above-described data of the heartbeat requires all of the data during sleep (from the start of sleeping to waking up), or requires data of a predetermined time period including at least the time point for which the sleep stage is to be estimated. Therefore, it has not been possible to estimate the sleep stage during a period where data is missing or in the near future for which data has not yet been generated.

The present invention has been proposed in view of the above-described conventional problems, and an object of the present invention is to make it possible to estimate the sleep stage at a time point where data does not exist.

Solution to Problem

In order to solve the above problems, according to the present invention, an acquiring unit configured to acquire biological data indicating a wave of a heartbeat; a parameter estimating unit configured to estimate a parameter by using the biological data, with respect to a mathematical expression defining a value with respect to elapsed time of a medium frequency component of the wave of the heartbeat by using the parameter; and a sleep stage estimating unit configured to estimate a sleep stage from the value of the medium frequency component at any time point, based on the mathematical expression to which the estimated parameter is applied, are included.

Advantageous Effects of Invention

According to the present invention, the estimation of the sleep stage at a time point where data does not exist, is enabled.

BRIEF DESCRIPTION OF DRAWINGS

FIG. 3 is a diagram showing an example of a definition of the wave of the heartbeat and parameter estimation.

DESCRIPTION OF EMBODIMENTS

A description of preferred embodiments of the present invention will be described below.

<Configuration>

Figure 1:
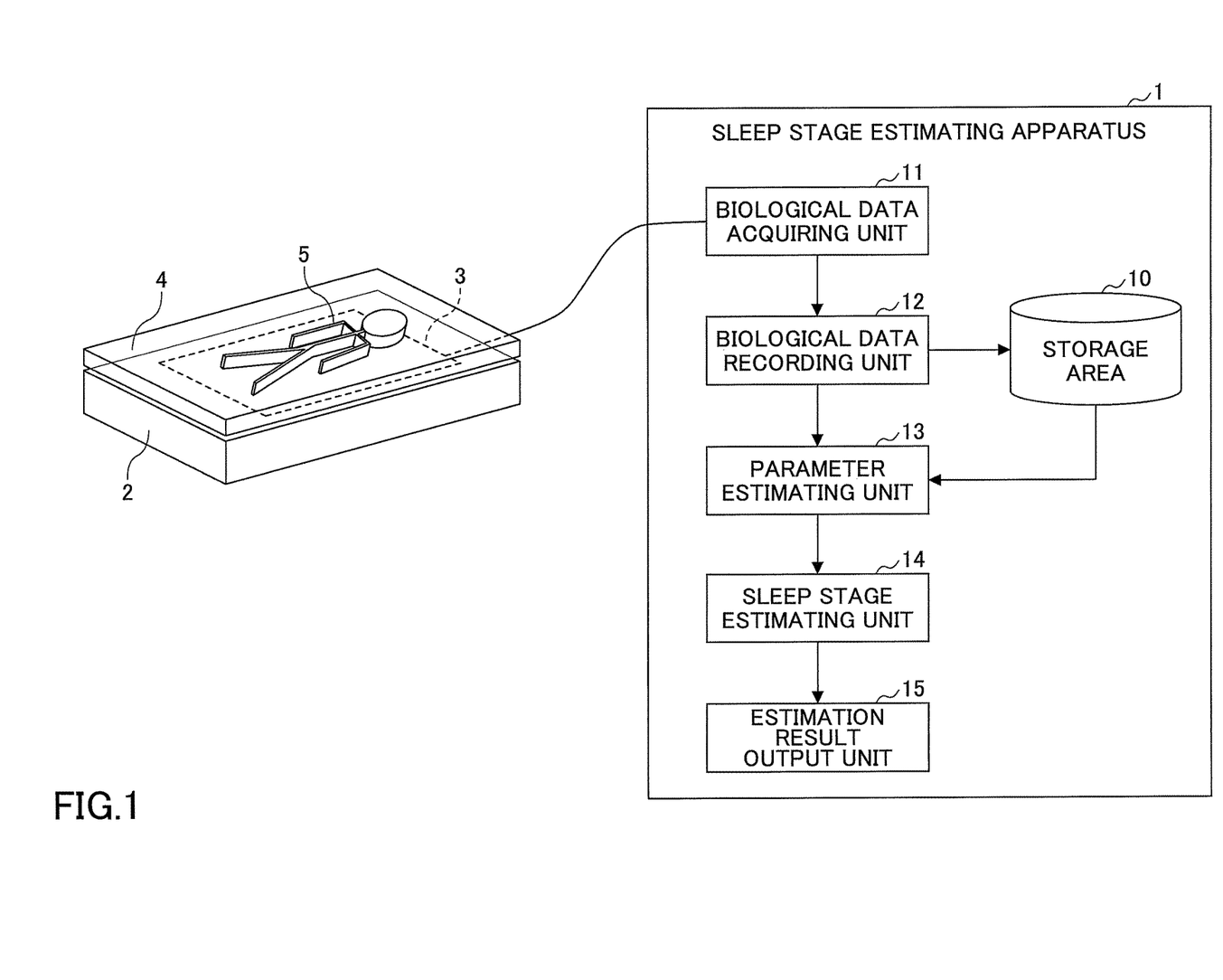
FIG. 1 is a diagram showing a configuration example of a sleep stage estimating apparatus according to an embodiment of the present invention.

FIG. 1 is a diagram showing a configuration example of a sleep stage estimating apparatus 1 according to an embodiment of the present invention.

In FIG. 1, the sleep stage estimating apparatus 1 includes a biological data acquiring unit 11, a biological data recording unit 12, a parameter estimating unit 13, a sleep stage estimating unit 14, and an estimation result output unit 15.

The biological data acquiring unit 11 has a function of acquiring biological data from an unrestrained type sensor 3, etc., installed between a bed 2 and a mattress 4 where a subject 5 sleeps. The unrestrained type sensor 3 outputs biological data indicating the heartbeat and waves of other body movements of the subject 5, and is formed of a sheet-like pressure sensor, etc.

The biological data recording unit 12 has a function of recording biological data, acquired by the biological data acquiring unit 11, in a storage area 10. In the biological data recorded in the storage area 10, the time when the biological data is acquired, is associated with a value of the wave magnitude of the heartbeat at the time when the biological data is acquired.

The parameter estimating unit 13 has a function of estimating, at a predetermined timing, a parameter of a mathematical expression defining a medium frequency component of a heartbeat wave by using a parameter, based on the biological data recorded in the storage area 10. By estimating the parameter, it is possible to estimate the value of the medium frequency component of the heartbeat wave at any time point during sleep.

The sleep stage estimating unit 14 has a function of estimating the sleep stage from the value of the medium frequency component of the heartbeat wave at any time point, by applying the parameter estimated by the parameter estimating unit 13 to the mathematical expression. Note that the fact that the medium frequency component of the heartbeat wave indicates the sleep stage, is based on the findings described in Non Patent Literature 5 and Non Patent Literature 6 described above.

The estimation result output unit 15 has a function of outputting the sleep stage estimated by the sleep stage estimating unit 14 outside, by displaying the estimated sleep stage, etc.

<Operations>

Figure 2:
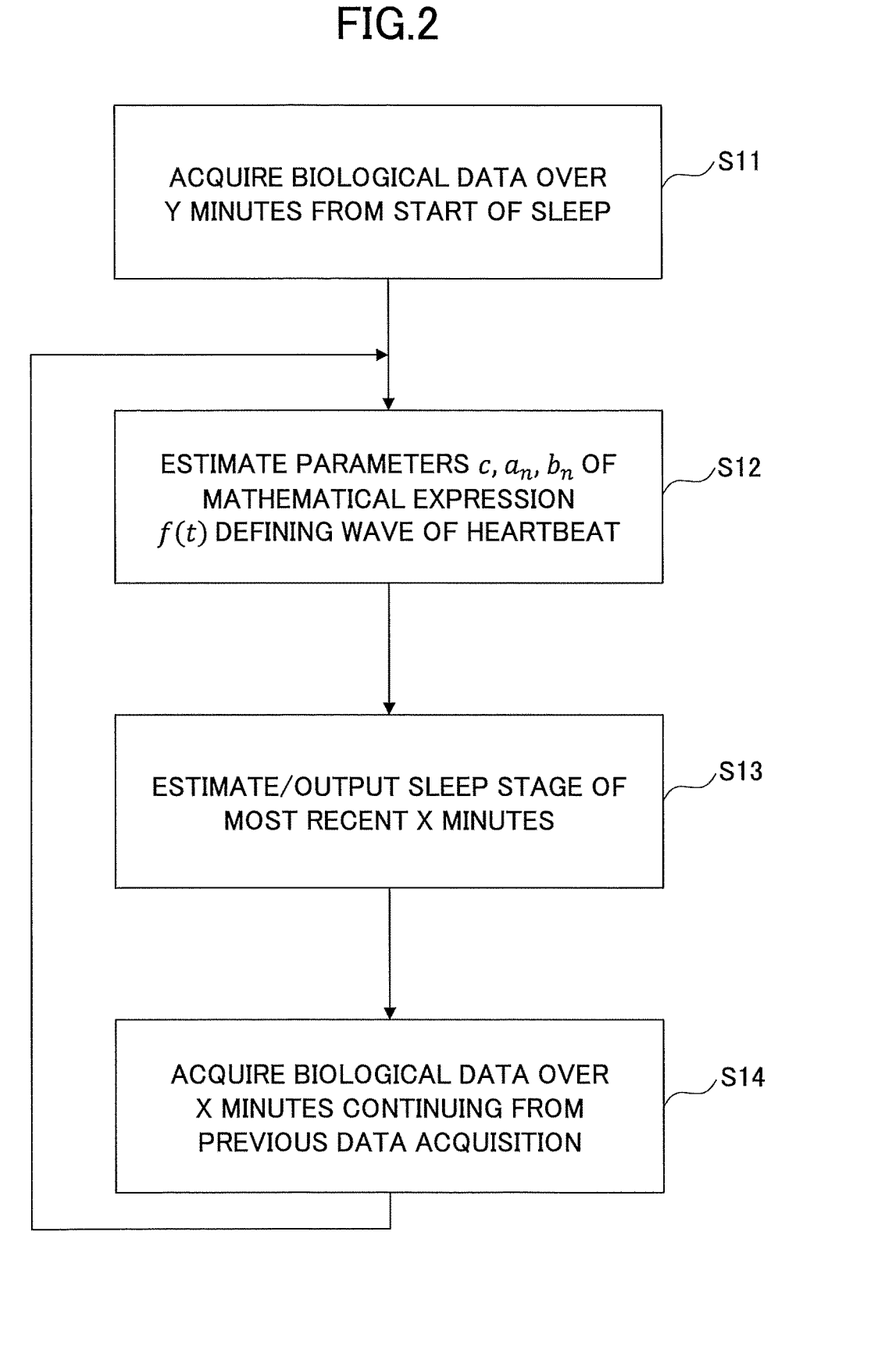
FIG. 2 is a flowchart showing a process example of an embodiment.

FIG. 2 is a flowchart showing a process example of the above embodiment, which is an example of estimating the sleep stage at the present time point in a real-time manner.

In FIG. 2, the biological data acquiring unit 11 acquires biological data for over a predetermined Y minute period, from when the subject 5 starts sleeping, and the biological data recording unit 12 records the acquired biological data in the storage area 10 (step S11). The start of sleep of the subject 5 is the time point when the subject 5 has started to go to bed. This time point may be determined by an instruction input by an administrator, and may also be automatically determined by a signal change of the unrestrained type sensor 3 or other sensors, etc. The reason for acquiring biological data for a predetermined Y minute period from the start of sleep is that sufficient estimation cannot be performed unless a certain number of biological data items are collected. Although sufficient estimation cannot be made before the elapse of Y minutes, a long time is not required, so in this respect, sufficient real-time properties can be secured.

Next, the parameter estimating unit 13 estimates parameters $c$, $a_n$, $b_n$ of a mathematical expression f (t) defining the heartbeat wave (step S12).

In the upper part of FIG. 3, an example of a definition expression of the mathematical expression f (t) is shown. The definition expression is expressed as a combination of a basic cycle L (corresponding to a bedtime period from the start of sleeping to waking up) and a wave of a cycle that is one "n" th of the basic cycle L. The parameter c is a constant term, the parameter $a_n$ is a coefficient of a cosine component, and the parameter $b_n$ is a coefficient of a sine component. Note that when the time t is in units of seconds, for example, the basic cycle L is fixed at $2^{15}$ seconds (approximately 9 hours), the lower limit value of n is fixed at 1, and the upper limit value N of n is fixed at 25, for example; however, these values may be changed according to experiments and operations.

The lower part of FIG. 3 shows a calculation expression for the parameters $c$, $a_n$, $b_n$. HR (t) is a value of biological data at the time t. m is for simplifying the notation as shown below the calculation expression. T is the time from the start of sleeping until the present time point.

Figure 4:
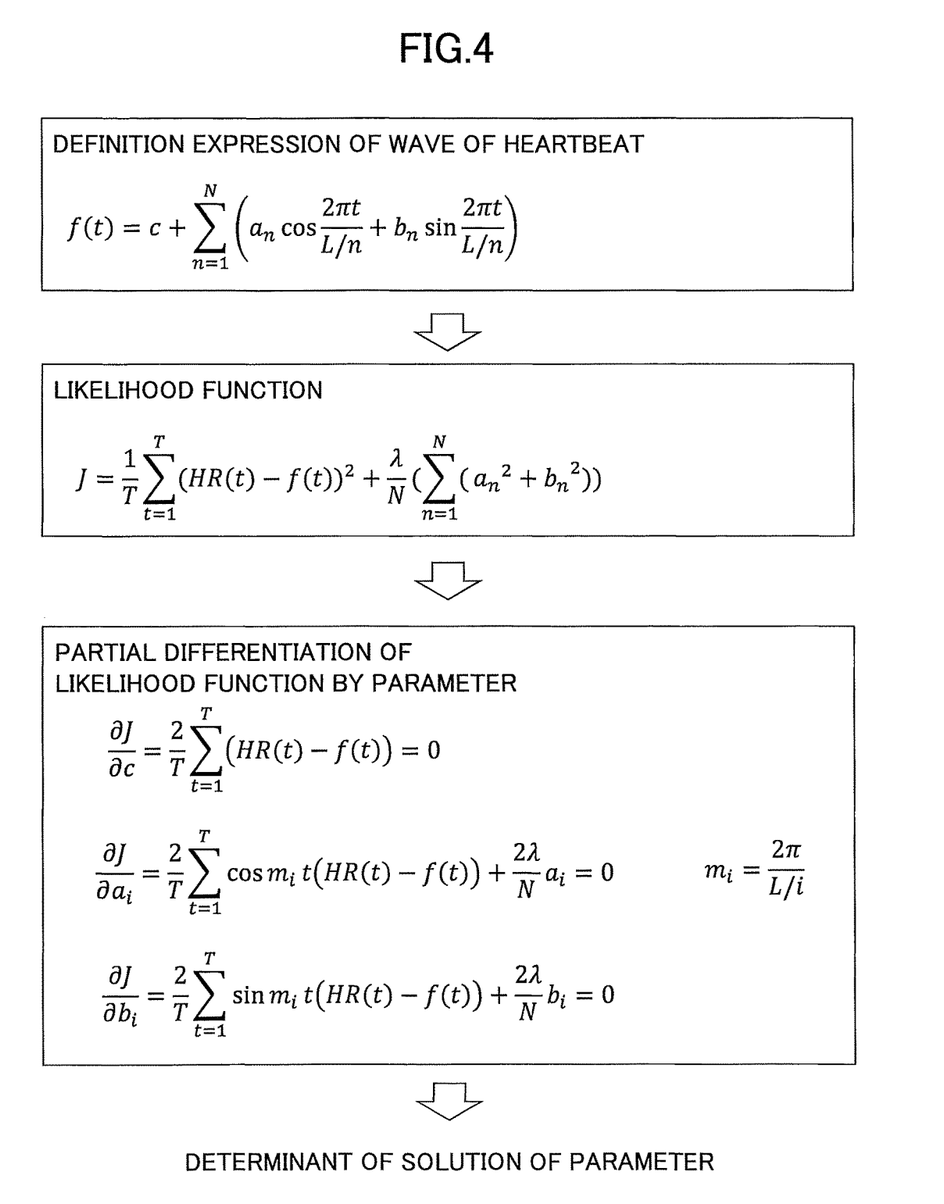
FIG. 4 is a diagram showing an example of the derivation of a calculation expression of parameter estimation.

Here, the derivation of the parameter calculation expression (lower part of FIG. 3) will be described. In FIG. 4, the sum of the square of the difference between a value f (t) of the heartbeat wave and the value HR (t) of the biological data that is an actually measured value, is divided by the time T, and the regular term is added, to obtain a likelihood function J. The regular term is for avoiding overfitting in a case where there is a small number of biometric data items HR (t). As a coefficient $\lambda$, an appropriate value such as 1 is set according to experiments or operations.

In order to obtain the parameters c, $a_n$, $b_n$ by which the mathematical expression f (t) defining the heartbeat wave most closely matches the value HR (t) of the biological data that is the actually measured value, zero is set for the likelihood function J partially differentiated by the parameters c, $a_n$, $b_n$, respectively. Accordingly, it is possible to obtain the same number of expressions as the number of the parameters c, $a_n$, $b_n$. The determinant of the solution of the simultaneous equation is the calculation expression of the parameters (lower part of FIG. 3).

Figure 5:
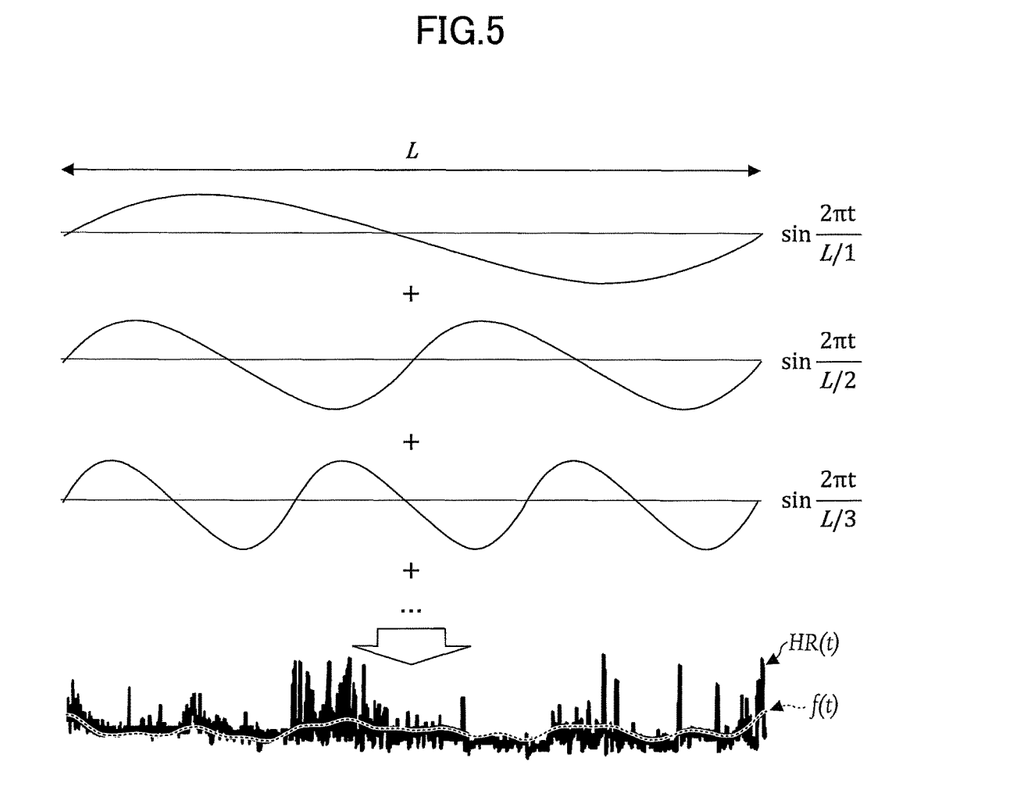
FIG. 5 shows a conceptual diagram of parameter estimation.

FIG. 5 shows a conceptual diagram of the above-described parameter estimation, for obtaining the parameters c, $a_n$, $b_n$ by which f (t), which is expressed as a combination of the basic cycle L and the wave of a cycle that is one "n" th of the basic cycle L, most closely matches the value HR (t) of the biological data that is the actually measured value. Note that during a time L corresponding to the bedtime period from the start of sleeping until waking up, the actual calculation is performed after Y minutes has elapsed from the start of sleeping. The f (t) value that is valid for the entire period of the time L, is obtained based on the value HR (t) of the biological data that is the actually measured value from the start of sleeping to the time point where Y minutes have elapsed.

Next, referring back to FIG. 2, the sleep stage estimating unit 14 applies the parameters c, $a_n$, $b_n$ estimated by the parameter estimating unit 13 to the mathematical expression f (t), to estimate the sleep stage from the value of the medium frequency component of the heartbeat wave within the most recent X minutes from the present time point, and the estimation result output unit 15 outputs the estimated sleep stage (step S13).

Figure 6:
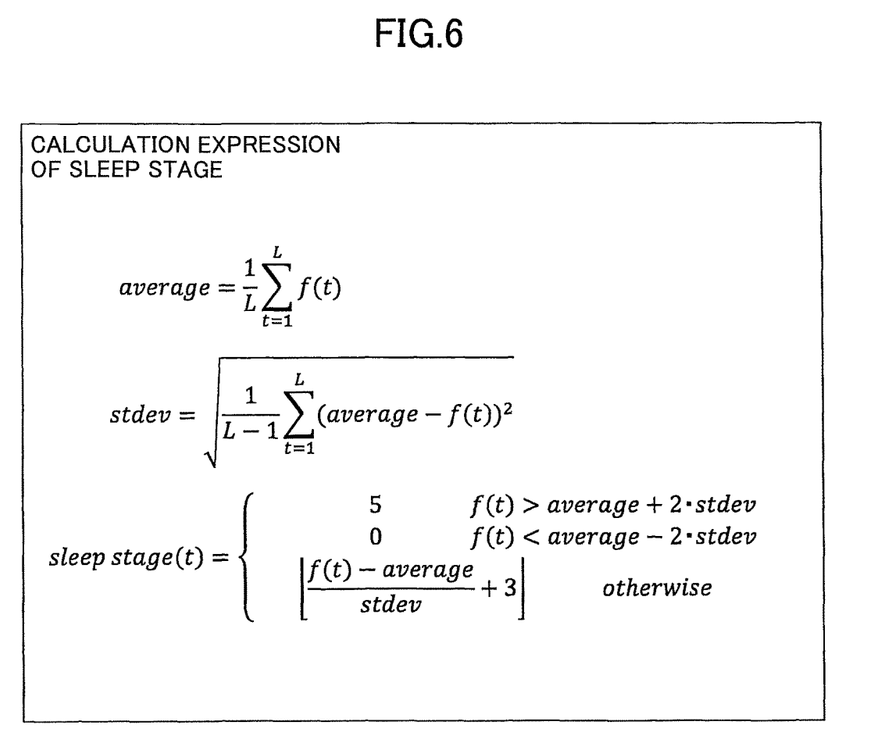
FIG. 6 is a diagram showing an example of a calculation expression of sleep stage estimation.

FIG. 6 is a diagram showing an example of a calculation expression of sleep stage estimation by the sleep stage estimating unit 14, in which the average value "average" and the standard deviation "stdev" of the value of the mathematical expression f (t) during the time L are calculated, and the sleep stage "sleep stage (t)" is calculated according to whether the representative value (the average value, etc.,) of f(t) within the most recent X minutes from the present time point is within "±stdev" from the average value "average", or within "±2·stdev" from the average value "average", or outside these ranges. Note that the correspondence between the sleep stages and the notations of Wake, Rem, Non-Rem 1, Non-Rem 2, Non-Rem 3, and Non-Rem 4 is as follows.

sleep stage (t)=5→Wake
sleep stage (t)=4→Rem
sleep stage (t)=3→Non-Rem 1
sleep stage (t)=2→Non-Rem 2
sleep stage (t)=1→Non-Rem 3
sleep stage (t)=0→Non-Rem 4

Note that instead of the above-described method of estimating the sleep stage, other conventional methods may be used.

Next, referring back to FIG. 2, the biological data acquiring unit 11 continues to acquire biological data for over X minutes from the previous data acquisition, and the biological data recording unit 12 records the acquired biological data in the storage area 10 (step S14).

Next, the process is repeated from the parameter estimation by the parameter estimating unit 13 (step S12), and the process is ended upon the subject waking up or the elapse of the time L. Note that even after the time L has elapsed, the parameter estimation may not be ended and may be continued.

Figure 7:
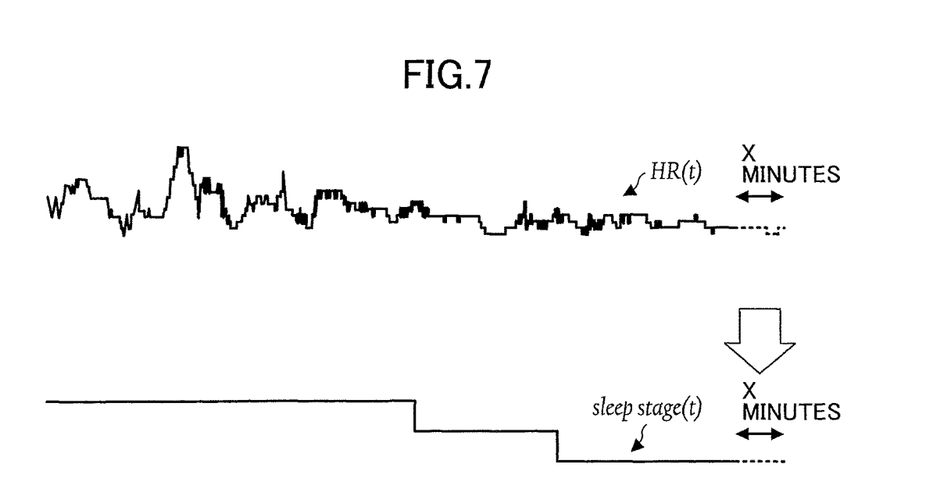
FIG. 7 is a diagram showing an example of the relationship between the addition of biological data and the sleep stage estimation.

FIG. 7 is a diagram showing an example of the relationship between the addition of biological data and the sleep stage estimation. At the stage of additionally acquiring the actually measured value HR (t) of X minutes, the sleep stage "sleep stage (t)" during this time is calculated and output. Note that the sleep stage "sleep stage (t)" that has been calculated and output in the past may change due to the fluctuation of the estimated values of the parameters c, $a_n$, $b_n$ due to the addition of the HR (t) of X minutes. However, it is not preferable to change a value that has already been output, and therefore past values will not be changed. However, in a case where it is important to correct and indicate the past sleep stage "sleep stage (t)" based on the latest actually measured value, the past value may be changed.

Figure 8:
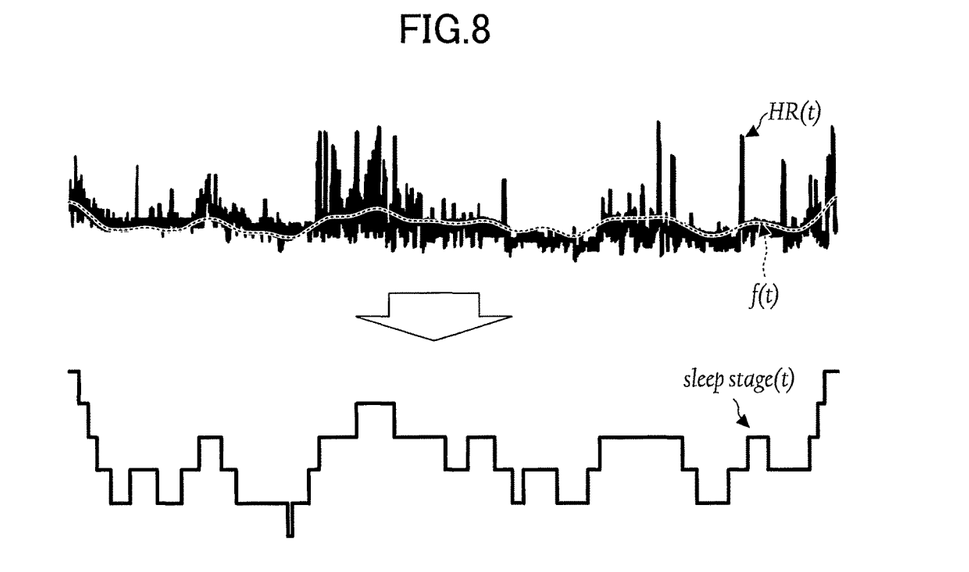
FIG. 8 shows an example of sleep stage estimation.

FIG. 8 shows an example of the relationship between f (t) estimated with respect to the actually measured value HR (t) and the sleep stage (t).

Note that in the example described above, on the premise of real-time estimation, the time of parameter estimation is assumed to be from the start of sleeping to the present time; however, it is also possible to estimate and output the sleep stage of the near future from the present time point to the bedtime L.

Furthermore, in the example described above, X minutes and Y minutes are described as the time of acquiring biological data; however, the acquisition of biological data is not limited to being in units of minutes, and appropriate values may be set according to experiments or operations.

Furthermore, it is also possible to estimate the sleep stage over the entire bedtime period, by using biological data of any period that is already acquired.

Furthermore, when the accuracy of estimation is partially different, by selectively using the biological data of a part with high estimation accuracy, the accuracy of estimation can be enhanced both overall and partially.

<Experimental Results>

FIGS. 9A to 9C and FIGS. 10A to 10C are diagrams showing experimental results.

Figure 9A:
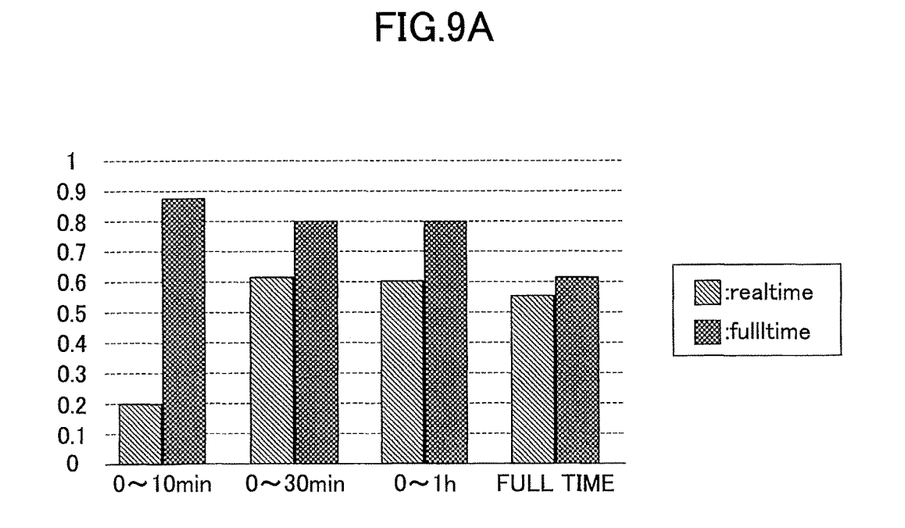
FIG. 9A is a diagram showing an experimental result (part 1).
Figure 9B:
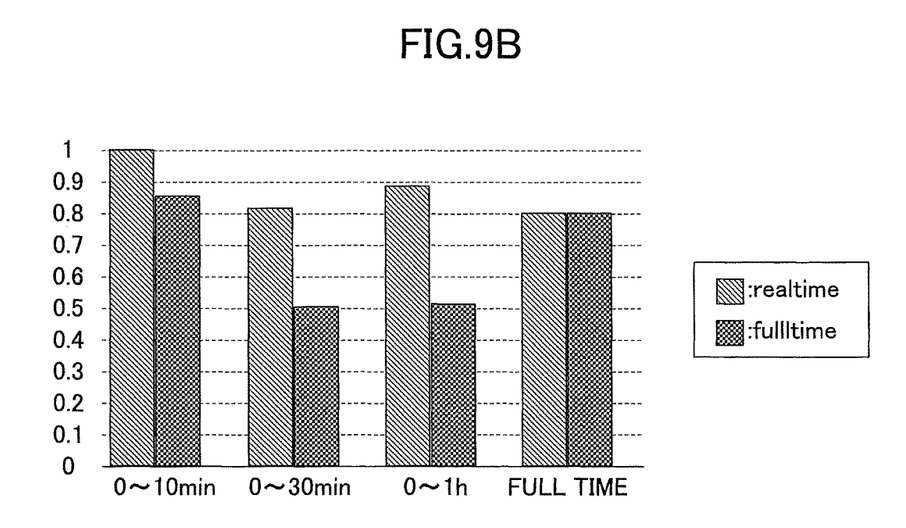
FIG. 9B is a diagram showing an experimental result (part 2).
Figure 9C:
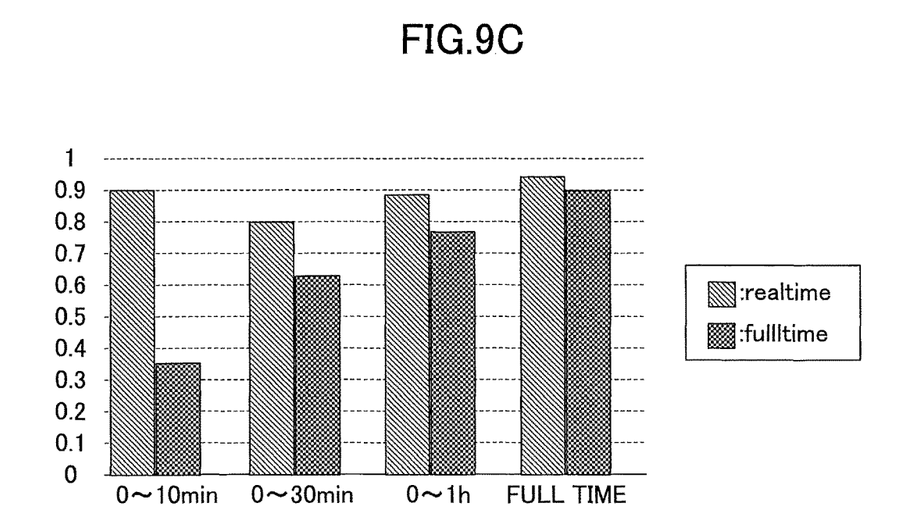
FIG. 9C is a diagram showing an experimental result (part 3).

Based on the premise that a sleep stage "Wake" is included and a deviation of one stage is allowed (a variation of approximately one stage is meaningful in a medical examination but can often be ignored in determining the sleeping state of a subject), FIGS. 9A to 9C show experimental results confirming the coincidence rate of real time estimation (real time) and estimation based on the data of the entire period (full time), with respect to a sleep polygraph test with the passage of time. FIG. 9A shows results for Mr. A, FIG. 9B shows results for Mr. B, and FIG. 9C shows results for Mr. C.

Referring to FIG. 9A, it was found that, for real time estimation, although the coincidence rate was initially low, the coincidence rate increased with the passage of time. For the estimation of the entire period, the coincidence rate was high from the beginning, and the coincidence rate tended to slightly decrease with the passage of time.

Referring to FIG. 9B, it was found that, for the real time estimation, the coincidence rate was high from the beginning, and with the passage of time, the coincidence rate slightly decreased and fluctuated. For the estimation of the entire period, the coincidence rate was high from the beginning, and with the passage of time, the coincidence rate tended to slightly decrease and fluctuate.

Referring to FIG. 9C, it was found that, for the real time estimation, the coincidence rate was high from the beginning, and with the passage of time, the coincidence rate slightly fluctuated. For the estimation of the entire period, the coincidence rate was initially low, and with the passage of time, the coincidence rate tended to rise.

Figure 10A:
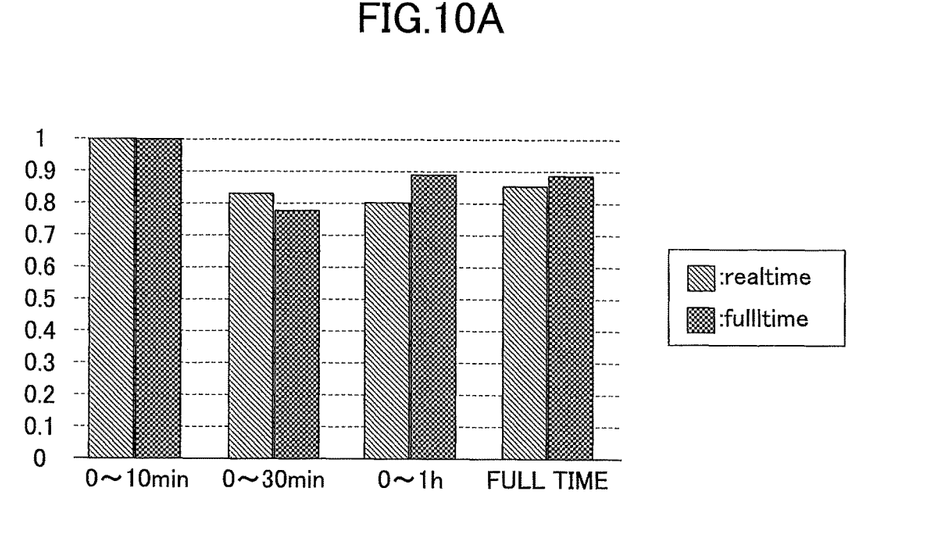
FIG. 10A is a diagram showing an experimental result (part 4).
Figure 10B:
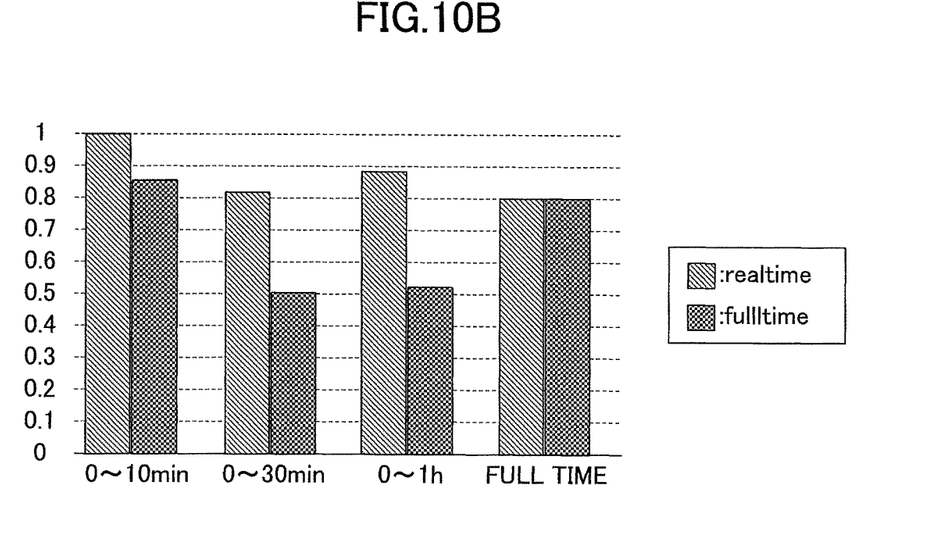
FIG. 10B is a diagram showing an experimental result (part 5).
Figure 10C:
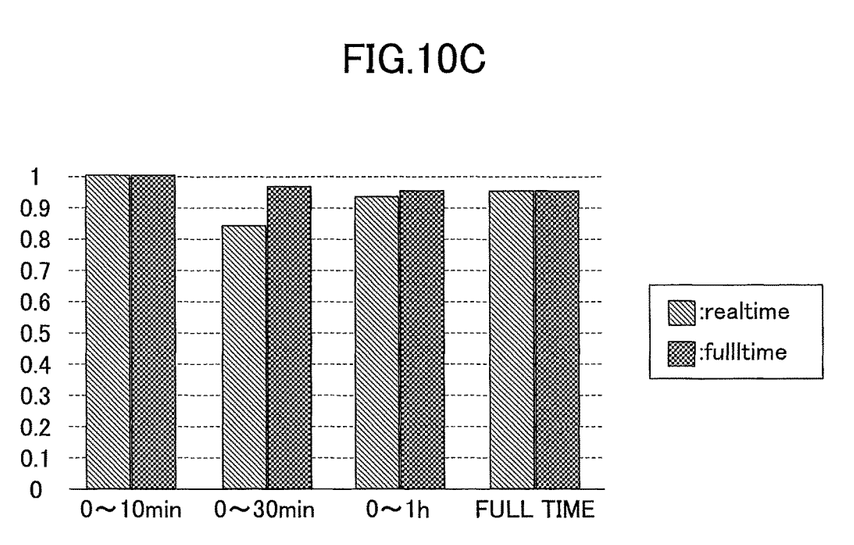
FIG. 10C is a diagram showing an experimental result (part 6).

FIGS. 10A to 10O show experimental results confirming the coincidence rate of real time estimation (real time) and estimation based on the data of the entire period (full time), with respect to a sleep polygraph test with the passage of time, on the premise that a deviation of one stage is allowed except for the sleep stage "Wake". FIG. 10A shows results for Mr. A, FIG. 10B shows results for Mr. B, and FIG. 10C shows results for Mr. C. Referring to each of FIGS. 10A to 10O, both the real time estimation and the estimation of the entire period had high coincidence rates from the beginning, and although there were slight fluctuations, preferable estimations were obtained.

<Applications>

The sleep stage estimation according to the present embodiment can be used in the following scenes.

(1) Sleep monitoring system leading to good sleeping

For people suffering with sleeping including insomnia, by using the present technique, it is possible to estimate the sleep stage in a real-time manner and lead the person to good sleeping, by delaying the rhythm of music, etc., so that the sleep becomes deep when the sleep is light. This technique can also be utilized for resolving jet lags, etc.

(2) Monitoring sleep of residents of nursing and personal care facilities

For a care person, the task of changing diapers is hard work and it is an unpleasant time for residents. In particular, since changing diapers at "midnight" is difficult, by using the present technique, it is possible to estimate the sleep stage in a real-time manner, and change the diaper when the resident is sleeping deeply, so that it is possible to exchange diapers without being noticed by resident.

Furthermore, when waking up a resident, it is possible to wake up the resident when the sleep is light, such that both the care person and the resident can smoothly perform the task of waking up.

SUMMARY

As described above, according to the present embodiment, it is possible to estimate the sleep stage at a time point for which there is no data.

The present invention is described above according to preferred embodiments of the present invention. Here, the present invention is described by indicating particular specific examples; however, it is obvious that variations and modifications may be made to the specific examples without departing from the spirit and scope of the claims of the present invention. That is, the present invention is not to be construed as being limited to the details of the specific examples and attached drawings.

The present international patent application claims the benefit of priority of Japanese Priority Patent Application No. 2015-55080, filed on Mar. 18, 2015, the contents of which are incorporated herein by reference in their entirety.

REFERENCE SIGNS LIST 1 sleep stage estimating apparatus
10 storage area
11 biological data acquiring unit
12 biological data recording unit
13 parameter estimating unit
14 sleep stage estimating unit
15 estimation result output unit
2 bed
3 unrestrained type sensor
4 mattress
5 subject

The invention claimed is:

1. A sleep stage estimating apparatus comprising:
an acquiring unit configured to constantly acquire real-time biological data indicating a wave of a heartbeat;
a parameter estimating unit configured to constantly estimate a real-time parameter at a particular point in time while acquiring the real-time biological data by using the constantly acquired real-time biological data, with respect to a mathematical expression defining a medium frequency component of the wave of the heartbeat by using the real-time parameter; and
a sleep stage estimating unit configured to estimate a sleep stage from the value of the medium frequency component at any time point, based on the mathematical expression to which the estimated parameter is applied.

2. The sleep stage estimating apparatus according to claim 1, wherein the parameter estimating unit and the sleep stage estimating unit estimate, for a first time, at a time point when the acquiring unit has acquired the biological data over a first predetermined time period, and subsequently estimate every time a second predetermined time period elapses.

3. The sleep stage estimating apparatus according to claim 1, wherein the parameter estimating unit is configured to estimate a constant term c, a coefficient of a cosine component $a_n$, and a coefficient of a sine component $b_n$ in an expression of a wave of a heartbeat f(t), wherein $$f(t) = c + \sum_{n=1}^{N}\left(a_n \cos \frac{2\pi t}{L/n} + b_n \sin \frac{2\pi t}{L/n}\right),$$

L being defined as a bedtime period from a start of sleeping to waking up,
the N being an upper limit value of n.

4. The sleep stage estimating apparatus according to claim 3, wherein the parameter estimating unit is configured to estimate the constant term c, the coefficient of a cosine component $a_n$, and the coefficient of a sine component $b_n$ by acquiring a determinant of a solution of a simultaneous equation including an equation that is generated by partially differentiating a likelihood function J by the constant term c, the coefficient of a cosine component $a_n$, and the coefficient of a sine component $b_n$, respectively, wherein $$J = \frac{1}{T}\sum_{t=1}^{T}(HR(t) - f(t))^2 + \frac{\lambda}{N}\left(\sum_{n=1}^{N}(a_n^2 + b_n^2)\right)$$

$$\frac{\partial J}{\partial c} = \frac{2}{T}\sum_{t=1}^{T}(HR(t) - f(t)) = 0$$

$$\frac{\partial J}{\partial a_i} = \frac{2}{T}\sum_{t=1}^{T}\cos m_i t(HR(t) - f(t)) + \frac{2\lambda}{N}a_i = 0 \quad m_i = \frac{2\pi}{L/i}$$

-continued $$\frac{\partial J}{\partial b_i} = \frac{2}{T}\sum_{t=1}^{T} \sin m_i t(HR(t) - f(t)) + \frac{2\lambda}{N} b_i = 0,$$

the HR (t) being a value of biological data at the time t,
the λ being a coefficient that is set according to experiments or operations, and
the T being time elapsed from a start of sleeping until present time point.

5. A biological data estimating apparatus comprising:
an acquiring unit configured to constantly acquire real-time biological data indicating a wave of a heartbeat;
a parameter estimating unit configured to constantly estimate a real-time parameter at a particular point in time while acquiring the real-time biological data by using the constantly acquired real-time biological data, with respect to a mathematical expression defining a medium frequency component of the wave of the heartbeat by using the real-time parameter; and
a data generating unit configured to generate data of a value of the medium frequency component at any time point for estimating the biological data, based on the mathematical expression to which the estimated parameter is applied.

6. A sleep stage estimating method executed by a sleep stage estimating apparatus, the sleep stage estimating method comprising:
an acquiring step of constantly acquiring real-time biological data indicating a wave of a heartbeat;
a parameter estimating step of constantly estimating a real-time parameter at a particular point in time while acquiring the real-time biological data by using the constantly acquired real-time biological data, with respect to a mathematical expression defining a medium frequency component of the wave of the heartbeat by using the real-time parameter; and
a sleep stage estimating step of estimating a sleep stage from a value of the medium frequency component at any time point, based on the mathematical expression to which the estimated parameter is applied.

7. A biological data estimating method executed by a biological data estimating apparatus, the biological data estimating method comprising:
an acquiring step of constantly acquiring real-time biological data indicating a wave of a heartbeat;
a parameter estimating step of constantly estimating a real-time parameter at a particular point in time while acquiring the real-time biological data by using the constantly acquired real-time biological data, with respect to a mathematical expression defining a medium frequency component of the wave of the heartbeat by using the real-time parameter; and
a data generating step of generating data of a value of the medium frequency component at any time point for estimating the biological data, based on the mathematical expression to which the estimated parameter is applied.

8. A non-transitory computer-readable recording medium storing a sleep stage estimating program that causes a computer to execute a process, the process comprising:
constantly acquiring real-time biological data indicating a wave of a heartbeat;
constantly estimating a real-time parameter at a particular point in time while acquiring the real-time biological data by using the constantly acquired real-time biological data, with respect to a mathematical expression defining a medium frequency component of the wave of the heartbeat by using the real-time parameter; and
estimating a sleep stage from a value of the medium frequency component at any time point, based on the mathematical expression to which the estimated parameter is applied.

9. A non-transitory computer-readable recording medium storing a biological data estimating program that causes a computer to execute a process, the process comprising:
constantly acquiring real-time biological data indicating a wave of a heartbeat;
constantly estimating a real-time parameter at a particular point in time while acquiring the real-time biological data by using the constantly acquired real-time biological data, with respect to a mathematical expression a medium frequency component of the wave of the heartbeat by using the real-time parameter; and
generating data of a value of the medium frequency component at any time point for estimating the biological data, based on the mathematical expression to which the estimated parameter is applied.

* * * * *